US011564634B2

(12) United States Patent
Vonikakis et al.

(10) Patent No.: US 11,564,634 B2
(45) Date of Patent: Jan. 31, 2023

(54) DETERMINING HEALTH STATE OF INDIVIDUALS

(71) Applicant: PANASONIC INTELLECTUAL PROPERTY MANAGEMENT CO., LTD., Osaka (JP)

(72) Inventors: Vasileios Vonikakis, Singapore (SG); Ariel Beck, Singapore (SG); Khai Jun Kek, Batu Pahat (MY)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 904 days.

(21) Appl. No.: 16/366,939

(22) Filed: Mar. 27, 2019

(65) Prior Publication Data
US 2020/0305801 A1    Oct. 1, 2020

(51) Int. Cl.
*A61B 5/00* (2006.01)
*A61B 5/0205* (2006.01)
*A61B 5/11* (2006.01)
*A61B 5/117* (2016.01)
*A61B 5/024* (2006.01)

(52) U.S. Cl.
CPC .......... *A61B 5/7275* (2013.01); *A61B 5/0077* (2013.01); *A61B 5/0205* (2013.01); *A61B 5/117* (2013.01); *A61B 5/1118* (2013.01); *A61B 5/4872* (2013.01); *A61B 5/7264* (2013.01); *A61B 5/024* (2013.01); *A61B 2562/0247* (2013.01)

(58) Field of Classification Search
CPC ... A61B 5/7275; A61B 5/0077; A61B 5/0205; A61B 5/1118; A61B 5/117; A61B 5/4872; A61B 5/7264; A61B 5/024
See application file for complete search history.

(56) References Cited

U.S. PATENT DOCUMENTS

| 2008/0162352 | A1* | 7/2008 | Gizewski | G16Z 99/00 705/50 |
| 2013/0012790 | A1* | 1/2013 | Horseman | A61B 5/6891 600/301 |
| 2015/0037771 | A1* | 2/2015 | Kaleal, III | G16H 20/30 434/257 |

FOREIGN PATENT DOCUMENTS

JP    2018-138449 A    9/2018

* cited by examiner

*Primary Examiner* — Joseph M Dietrich
(74) *Attorney, Agent, or Firm* — McDermott Will & Emery LLP

(57) ABSTRACT

The present subject matter discloses a system(s) and a method(s) for determining a health state of an individual. According to an embodiment, a method comprises measuring, by a heart rate sensor, a heart rate of the individual during operation within the environment. The method further comprises outputting, by a pressure sensing platform, pressure data of the individual. Further, the method comprises outputting, by an image capturing device, image data of the individual. The method further comprises inferring, by a processing unit, an amount of fat of the individual in the image data. The method further comprises updating, by the processing unit, the amount of fat of the individual using the pressure data. The method further comprises controlling, by the processing unit, a threshold for determining the health state of the individual, using the amount of fat and the heart rate of the individual.

20 Claims, 8 Drawing Sheets

DETERMINING HEALTH STATE OF INDIVIDUALS

TECHNICAL FIELD

The present subject matter relates generally to health monitoring and more particularly to determining health state of individuals.

BACKGROUND

With advancement in technology, various techniques for monitoring health of individuals within an environment are nowadays implemented. Such techniques typically involve measuring a physiological parameter, such as a heart rate, of the individual and then assessing the health of the individual based on the measured heart rate. For assessing the health, the value of the parameter is typically compared with a threshold value. Based on a deviation of the measured value of the parameter from the threshold, the health state of the individual is determined.

In most conventional techniques, the threshold against which the measured value of the parameter is compared is static in nature. That is, the value of the threshold remains same for all individual. As is known, individuals differ in their physiological and biological characteristics. Accordingly, having a fixed threshold for determining health states of all individuals being monitored may not provide accurate health measurements.

Other conventional techniques of determining health states involve implementation of complex apparatuses/devices. Such techniques may employ obtrusive methods of determining health states. Accordingly, such techniques may require a clinical setup or even if implemented in routine spaces/environments, such techniques may hinder regular tasks/work of individuals. Accordingly, implementation of such devices in routine spaces/environments is not desirable.

SUMMARY

This summary is provided to introduce a selection of concepts in a simplified format that is further described in the detailed description of the present disclosure. This summary is neither intended to identify key inventive concepts of the disclosure nor is it intended for determining the scope of the invention or disclosure.

According to an embodiment of the present subject matter, a system for determining a health state of an individual is disclosed. The system comprises a heart rate sensor configured to measure a heart rate of the individual during operation within the environment. The system further comprises a pressure sensing platform configured to output pressure data of the individual. The system further comprises an image capturing device configured to output image data of the individual. The system further comprises a processing unit communicatively coupled to the heart rate sensor, the pressure sensing platform, and the image capturing device. The processing unit is configured to infer an amount of fat of the individual in the image data. Further, the processing unit is configured to update the amount of fat of the individual using the pressure data. Further, the processing unit is configured to control a threshold for determining the health state of the individual, using the amount of fat and the heart rate of the individual.

According to another embodiment of the present subject matter, a method of determining a health state of an individual is disclosed. The method comprises measuring, by a heart rate sensor, a heart rate of the individual during operation within the environment. The method further comprises outputting, by a pressure sensing platform, pressure data of the individual. Further, the method comprises outputting, by an image capturing device, image data of the individual. The method further comprises inferring, by a processing unit, an amount of fat of the individual in the image data. The method further comprises updating, by the processing unit, the amount of fat of the individual using the pressure data. The method further comprises controlling, by the processing unit, a threshold for determining the health state of the individual, using the amount of fat and the heart rate of the individual.

According to another embodiment of the present subject matter, non-transitory computer-readable medium having embodied thereon a computer program for executing a method implementable by a system is disclosed. The method of determining a health state of an individual is disclosed. The method comprises measuring, by a heart rate sensor, a heart rate of the individual during operation within the environment. The method further comprises outputting, by a pressure sensing platform, pressure data of the individual. Further, the method comprises outputting, by an image capturing device, image data of the individual. The method further comprises inferring, by a processing unit, an amount of fat of the individual in the image data. The method further comprises updating, by the processing unit, the amount of fat of the individual using the pressure data. The method further comprises controlling, by the processing unit, a threshold for determining the health state of the individual, using the amount of fat and the heart rate of the individual.

The objects and advantages of the embodiments will be realized and achieved at least by the elements, features, and combinations particularly pointed out in the claims. It is to be understood that both the foregoing general description and the following detailed description are representative and explanatory and are not restrictive of the invention, as claimed.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

Figure 1:
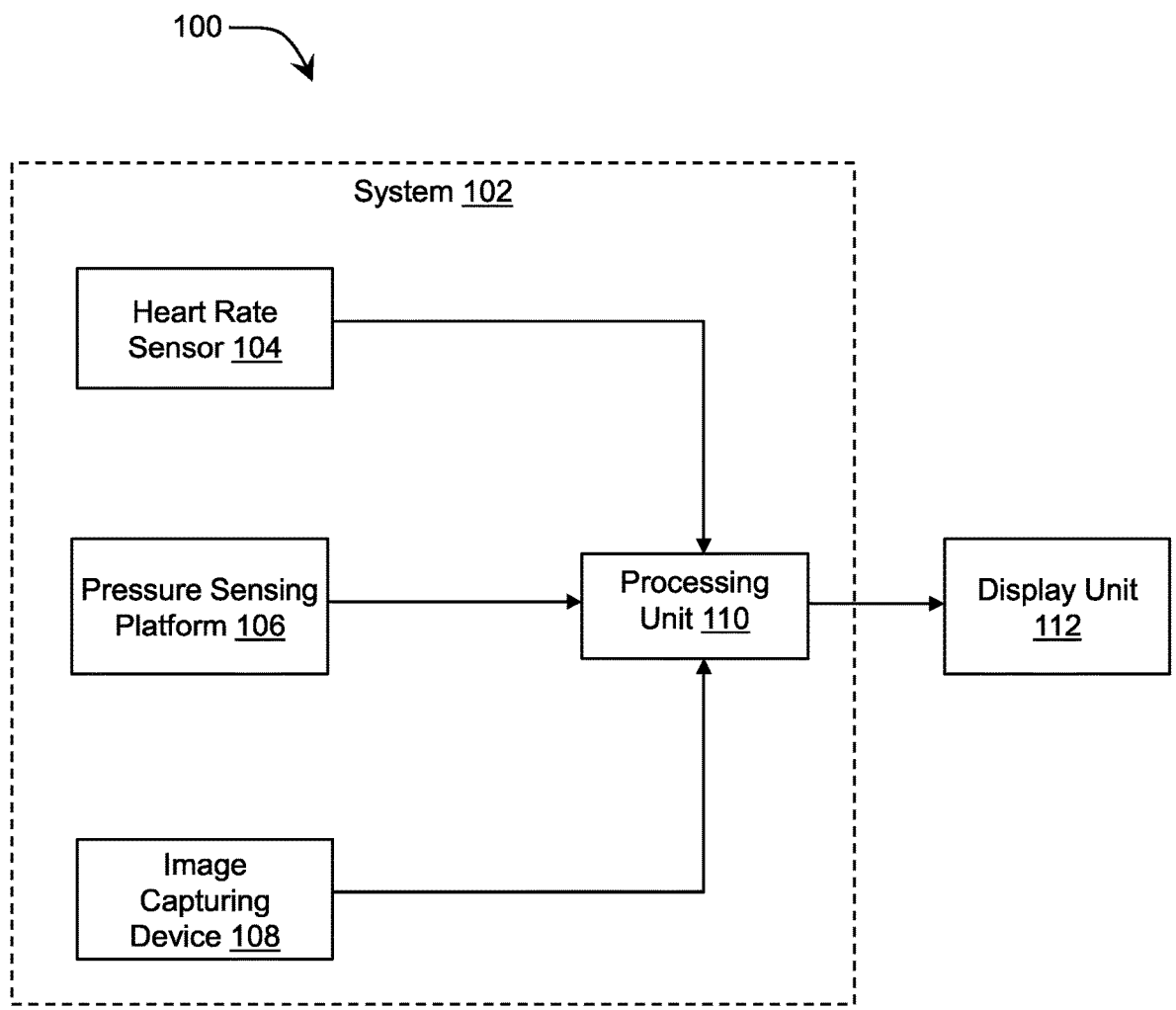
FIG. 1 illustrates an environment implementing a system for determining health state of individuals, according to one or more embodiments of the present subject matter.

The elements in the drawings are illustrated for simplicity and may not have been necessarily been drawn to scale. Furthermore, in terms of the construction of the device, one or more components of the device may have been represented in the drawings by conventional symbols, and the drawings may show only those specific details that are pertinent to understanding the embodiments of the present disclosure so as not to obscure the drawings with details that will be readily apparent to those of ordinary skill in the art having benefit of the description herein.

DETAILED DESCRIPTION

For the purpose of promoting an understanding of the principles of the present disclosure, reference will now be made to the embodiment illustrated in the drawings and specific language will be used to describe the same. It will be understood that no limitation of the scope of the present disclosure is thereby intended, such alterations and further modifications in the illustrated system, and such further applications of the principles of the present disclosure as illustrated therein being contemplated as would normally occur to one skilled in the art to which the present disclosure relates.

The foregoing general description and the following detailed description are explanatory of the present disclosure and are not intended to be restrictive thereof.

Reference throughout this specification to "an aspect", "another aspect" or similar language means that a particular feature, structure, or characteristic described in connection with the embodiment is included in at least one embodiment of the present disclosure. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or subsystems or elements or structures or components proceeded by "comprises . . . a" does not, without more constraints, preclude the existence of other devices or other subsystems or other elements or other structures or other components or additional devices or additional subsystems or additional elements or additional structures or additional components.

Unless otherwise defined, all technical and scientific terms used herein have the same meaning as commonly understood by one of ordinary skill in the art to which this present disclosure belongs. The system, methods, and examples provided herein are illustrative only and not intended to be limiting.

Conventional techniques of determining health states of individual involve measuring physiological parameters, for example, heart rate, and comparing such parameters with respective thresholds. Typically, such thresholds are static in nature. As physiological and biological characteristics vary from individual to individual, using a static threshold related to such characteristics for determining health state of individuals may provide inaccurate health measurements of individuals.

The present subject matter relates to system(s) and method(s) for determining health state of individuals. According to embodiments of the present subject matter, a health monitoring system, hereinafter referred to as "system", is configured to control a threshold for determining health state of an individual based on physiological characteristics and biological characteristics of the individual. In said embodiment, the threshold for determining the health state of the individual is controlled using the heart rate and an amount of fat of the individual. Controlling the threshold based on characteristics, such as heart rate and the amount of fat of the individual facilitates in increasing the accuracy of determination of the health state of individuals.

FIG. 1 illustrates an environment 100 implementing a system 102 for determining health state of individuals, according to one or more embodiments of the present subject matter. The environment 100, in an example, may be a closed space environment, such as an office space, a vehicle cabin, an airplane cabin, and the like. The system 102 may be implemented in such environments for determining a health state(s) of an individual(s) operating within such environments.

As depicted, the system 102 may include a heart rate sensor 104, a pressure sensing platform 106, an image capturing device 108, and a processing unit 110. In an example, the processing unit 110 is communicatively coupled to the heart rate sensor 104, the pressure sensing platform 106, and the image capturing device 108, for receiving data therefrom. The heart rate sensor 104, in an example, may be one of a contact-based or a contactless heart rate sensor. The pressure sensing platform 106 may be, for example, a pressure mat. The image capturing device 108, in an example, may be a camera, a Time of Flight (ToF) sensor, a depth sensor, an infrared camera, a thermal camera, and the like. For the sake of brevity, only one heart rate sensor 104, one pressure sensing platform 106, one image capturing device 108, and one processing unit 110 has been shown in the figure. The processor 202 can be a single processing unit or a number of units, all of which could include multiple computing units. The processor 202 may be implemented as one or more microprocessors, microcomputers, microcontrollers, digital signal processors, central processing units, graphical processing units, neural processing units, state machines, logic circuitries, and/or any devices that manipulate signals based on operational instructions. As would be understood, more than one of such aforementioned entities may be implemented to realize the aspects of the present subject matter. As further depicted, the environment 100 may include a display 112 communicatively coupled to the system 102. In an example, the system 102 is configured to display the health state of the individual and other data on the display 112.

In an example, a health state of an individual operating within the environment may be determined using the system 102. In said example, the individual may be seated on the pressure sensing platform 106 and subsequently the analysis related to the health state may be performed. According to an embodiment, the heart rate sensor 104 is configured to measure a heart rate of the individual during operation within the environment. In said embodiment, the heart rate sensor 104 outputs the measured heart rate as heart rate data. Furthermore, in said embodiment, the pressure sensing platform 106 is configured to output pressure data associated with the individual seated thereon. The pressure data may include, but is not limited to, information about the activated pressure cells of the pressure sensing platform 106, information about the percentage of area covered of the pressure sensing platform 106, and information about the overall pressure on the pressure sensing platform 106. Furthermore, in said embodiment, the image capturing device 108 is configured to output image data of the individual. The image data comprises a plurality of images of the individual.

Based on the heart rate, the pressure data, and the image data, the processing unit 110 is configured to infer an amount of fat of the individual. Subsequently, the processing unit 110 is configured to update the amount of fat based on the pressure data. The updation, as mentioned herein, may include, but is not limited to, verifying the inferred amount of fat based on the pressure data, update the value of amount of fat in case of any discrepancy, and/or retaining the value of amount of fat in case of non-discrepancy. Post updation of the amount of fat, the processing unit 110 is configured to control a threshold to determine a health state of the individual, using the heart rate and the amount of fat of the individual. The threshold, as used herein, indicates a threshold value of probability of the individual to have health issues. In an example, the controlling of the threshold may be inversely proportional to the measured heart rate and the amount of fat. For instance, for same age group individuals, it may be the case that an obese person has a higher resting heart rate and higher amount of fat, and a fit person has a lower resting heart rate and lower amount of fat. Accordingly, when the analysis is performed in respect of the obese person, the threshold may be lowered and when the analysis is performed in respect of the fit person, the threshold may be increased.

Subsequent to the controlling of the threshold, the processing unit 110 is configured to determine a first probability, a second probability, and a third probability of having health issues, in respect of the individual. In an example, the first probability of having health issues is determined based on the measured heart rate of the individual. In an example, the second probability of having health issues is determined based on an age, a race, a gender, a BMI, and an identity of the individual. In an example, the third probability of having health issues is determined based on at least one activity, for example, facial activity, such as facial expressions, and body activity, such as body part gestures, of the individual. In addition to the aforementioned probabilities, the processing unit 110 is configured to infer movement of the individual, as performed over a predetermined period, using the image data. For instance, the processing unit 110 may infer that the individual is moving/not moving for the predetermined time.

Based on at least one of the first probability, the second probability, the third probability, and the inferred movement, the system 102 is configured to determine the health state of the individual. In an example, the health state may be a short term health state and may be determined using the first probability, the second probability, the third probability, and the movement of the individual. In an example, the health state may be a long term health state and may be determined using the second probability. In an example, the health state may be a grievous health state, for example, near to dead or dead, and may be determined using the first probability and the movement of the individual. The health state, as determined, may then be displayed on the display 112. Details of the determination of the health state are described in the following description.

Figure 2:
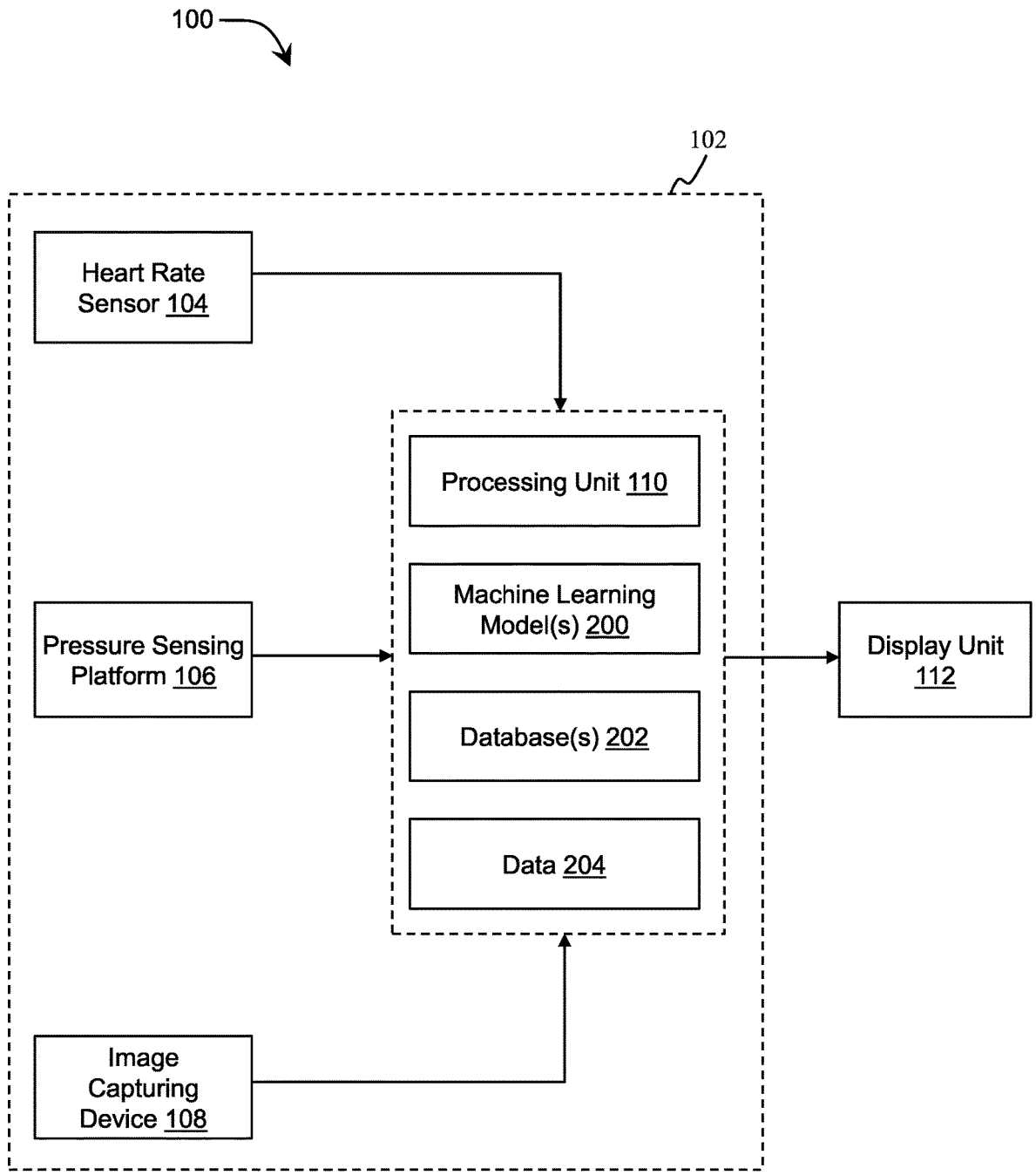
FIG. 2 illustrates a detailed schematic diagram of the system, in accordance with one or more embodiments of the present subject matter.

FIG. 2 illustrates a detailed schematic diagram of the system 102, in accordance with one or more embodiments of the present subject matter. As depicted, the system 102 may include one or more machine learning (ML) models 200. The ML models 200 may include ML models configured to analyze heart rate data, image data, and pressure data. Accordingly, in an example, the ML models 200 may be implemented on one or more of the heart rate data, the pressure data, and the image data. The outcome of such implementation may then be used by the processing unit 110 for determining the health state of the individual. Furthermore, as depicted, the system 102 may include or may be communicatively coupled to one or more databases 202. In an example, the databases 202 may include a first database, which may be a database of demographic medical studies. The databases 202 may further include a second database, which may be a database of historical medical data of individuals registered with the system 102. Furthermore, as depicted, the system 102 may include data 204. The data 204, amongst other things, is used to store data generated by the processing unit 110. Besides such data, the data 204 may include the data received from the heart rate sensor 104, the pressure sensing platform 106, and the image capturing device 108. Furthermore, the data 204 may include one or more of image processing algorithms, facial recognition algorithms, expert rules related to physiological and biological characteristics, data associated with physiological studies and biological studies, data of individuals registered with the system 102, and other data.

As mentioned above, the heart rate sensor 104 is configured to output the heart rate data including the measured heart rate of the individual. In an example, the heart rate sensor 104 may be configured to measure the heart rate of the individual for a predetermined time, say, three minutes or five minutes. The heart rate data, in one example, may be stored in the data 204. According to an embodiment, the processing unit 110 is configured to provide the heart rate data as in input to the ML models 200. As mentioned above, the ML models 200 may include ML models configured to analyze the heart rate data. Such ML models analyze the heart rate data and provide as an outcome, one or more probabilities of having health issues, as determined based on the heart rate data. For instance, the ML models may provide as an output, one or more of a probability of sudden cardiac death, a probability of 3H: hypertension, hyperlipidemia, hyperglycemia, a probability of coronary heart disease, a probability of diabetes, a probability of intoxication, and the like. In an alternate embodiment, the processing unit 110 may apply the expert rules, stored in the data 204, on the heart rate data to obtain as an outcome, the aforementioned probabilities. In another embodiment, a combination of the ML modes and the expert rules may be implemented for determining one or more of the aforementioned probabilities. Once the aforementioned probabilities are determined, the processing unit 110 may determine the first probability of having health issues based on one or more of the aforementioned probabilities.

As mentioned above, the image capturing device 108 is configured to output the image data of the individual. In an embodiment, the processing unit 110 is configured to determine one or more of the age, the race, the gender, the Body Mass Index (BMI), and the identity of the individual based on the image data. In said embodiment, the processing unit 110 may implement one or more of conventional techniques to analyze the image data for determining the age, the race, and the gender of the individual. Furthermore, the processing unit 110 may implement conventional face recognition and identification techniques for determining the identity of the individual. In a case where the processing unit 110 identifies the individual, i.e., the individual is a registered user, the processing unit 110 is configured to query the second database based on the identity of the individual. Subsequently, the processing unit 110 obtains one or more preconditions, if available, associated with the individual from the data 204. The one or more preconditions may include currently existing health conditions, such as heart patient, diabetic, and the like, of the individual. In another case where the individual is a first time user, he/she may be asked to create an account, or proceed as a guest. Furthermore, in said case, the individual may be asked to provide user information, such as height, weight, past health information, and the like. As may be noted, seeking of such information may form a part of initial registration of the individual with the system 102.

As further mentioned above, the pressure sensing platform is configured to output the pressure data of the individual. In an embodiment, the processing unit 110 is configured to determine the BMI of the individual using the image data and the pressure data. In said embodiment, the processing unit 110 is configured to extract a set of features from the image data and the pressure data. The set of features may include, but is not limited to, one or more face shape features, height features, weight features, and a ratio number associated with the individual. For extracting the face shape features and the height features, the processing unit 110 at first detects the face of the individual in the image data using the bounding box technique, in one example. Post detection of the face in the image, the height features are determined by computing the distance of the face from the bottom of the image. The face shape features, in an example, includes details of face alignment, for example, facial points, and details of jawline relative to facial parts. The facial points, in an example, are determined by implementing a face alignment algorithm. Accordingly, X and Y coordinates of the facial points of the individual are obtained. Subsequently, a mean of the X and Y coordinates of the facial points (excluding the jawline points) is computed. Thereafter, distances of the jawline points to the mean are computed and a summation thereof is obtained. This value is then divided by the number of points in the jawline to obtain the face shape features.

The weight features, in an example, includes the overall pressure and the percentage area covered by a rear body part(s) of the individual. The processing unit 110 determines said weight features from the pressure data received from the pressure sensing platform 106. As mentioned above, the pressure data may include, but is not limited to, information about the activated pressure cells of the pressure sensing platform 106, information about the percentage of area covered of the pressure sensing platform 106, and information about the overall pressure on the pressure sensing platform 106. In an example, an activation threshold may be defined for identifying which pressure cells of the pressure sensing platform 106 are activated and/or covered. Accordingly, by identifying the activated/covered pressure cells, the percentage area covered by the rear body part(s) of the individual may be determined. Furthermore, the readings from the activated/covered pressure cells are used to determine the overall pressure. The overall pressure may be used to identify the weight of the individual. Once the face shape features, height features, and weight features are determined, the processing unit 110 is configured to provide them as input to an ML model, from the ML models 200, that is configured to determine the BMI of individuals. Without limitation, the ML model may be one of a linear regression model or a neural network model. Based on the inputs, said ML model then determines the BMI of the individual being monitored.

Post determining/identifying the age, race, gender, BMI, and optionally, the preconditions associated with the individual, the processing unit 110 is configured to query the first database to determine the second probability of having health issues.

In an embodiment, the processing unit 110 is configured to identify an activity of the individual based on the image data. The activity, as used herein, may include the facial expressions and body part movement, or positioning thereof, of the individual. In said embodiment, the processing unit 110 may perform a body skeleton estimation using conventional techniques. As mentioned above, the facial alignment of the individual is also determined. Accordingly, using the facial alignment and a conventional technique, a first value indicative of the facial activity of the individual may be determined. The facial activity herein may be representative of pain expression on the face of the individual. In an example, a continuous value between zero and one may be determined. Furthermore, using the body skeleton estimation and a conventional technique, a second value indicative of the body activity of the individual may be determined. The body activity herein may be representative of health issues, for example, placement of hand on chest. In an example, a continuous value between zero and one may be determined. As a subsequent step, the processing unit 110 is configured to determine the third probability of having health issues based on the first value and the second value. In an example, the processing unit 110 may take an average of the first value and the second value to determine the third probability.

Furthermore, in an embodiment, the processing unit 110 is configured to infer the movement of the individual based on the image data. In said embodiment, the processing unit 110 may analyze the image data for a predetermined period, say, thirty seconds, to infer the movement of the individual. Accordingly, one of a movement and a non-movement of the individual may be learnt.

Subsequent to the above determinations and inferences, the processing unit 110 may then use one or more of the first, second, and third probability of having health issues, and the inferred movement of the individual to determine the health state of the individual.

In an embodiment, the processing unit 110 may determine a short term health state indicative of an immediate health state of the individual. In an example, the processing unit 110 may implement at least one of an ML model and a fuzzy logic technique to determine the short term health state of the individual. Referring to said embodiment, the processing unit 110 is configured to compare the first probability, the second probability, and the third probability of having health issues with the threshold. In a case where each of the first probability, the second probability, and the third probability of having health issues is equal to or greater than the threshold, the processing unit 110 may determine that the probability of having health issue is high. In an embodiment, in addition to the first probability, the second probability, and the third probability, the processing unit 110 may also determine the short term health state using the movement of the individual. For example, if the processing unit 110 ascertains that the individual is stationary for the predetermined period, the processing unit 110 may determine that the probability of having health issue is high.

In an embodiment, the processing unit 110 may determine a long term health state indicative of the health of the individual in future. In said embodiment, the processing unit 110 is configured to determine the long term health state based on the second probability. In other words, the processing unit 110 may output information, such as one or more health issues and the probabilities of individual having them in future.

In an embodiment, the processing unit 110 may determine the probability of the individual being in a grievous health state, for example, near to dead or dead. In an example, the processing unit 110 may implement at least one of an ML model and a fuzzy logic technique to determine the aforementioned health state of the individual. Referring to said implementation, the processing unit 110 is configured to compare the first probability of having health issues with the threshold. In a case where the first probability of having health issues is equal to or greater than the threshold, the processing unit 110 may determine that the probability of the individual being dead or nearly dead is high. In an embodiment, in addition to the first probability, the processing unit 110 may also use the movement of the individual, as inferred, for determining the aforementioned health state. For example, if the processing unit 110 ascertains that the individual is stationary for the predetermined period, the processing unit 110 may determine that the probability of individual being dead or nearly dead is high.

Upon determination of one or more of the aforementioned health states, in an embodiment, the system 102 may display information associated with the one or more of the health states of the individual on the display 112.

Figure 3:
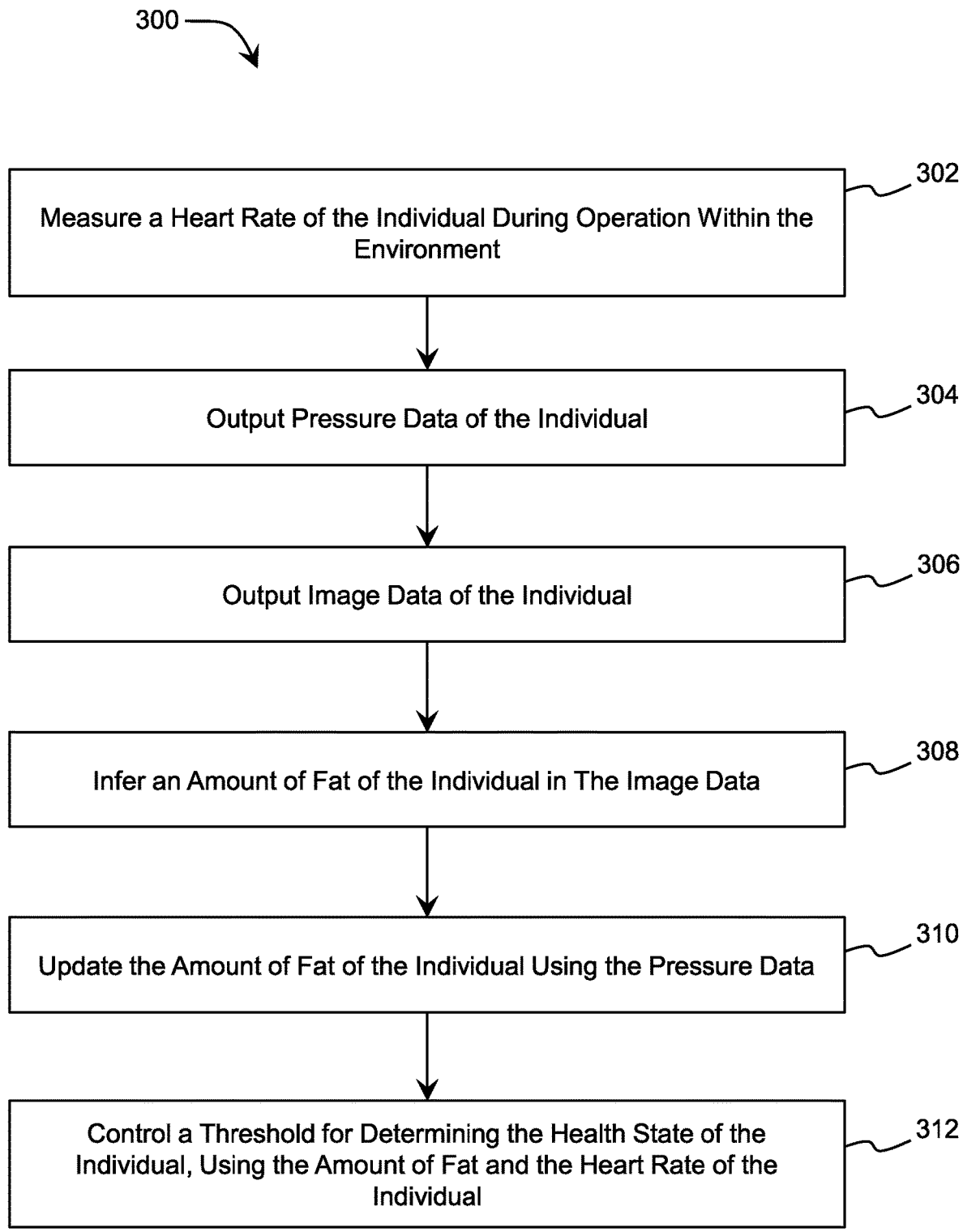
FIG. 3 illustrates a method of determining health state of individuals, according to an embodiment of the present subject matter.

FIG. 3 illustrates a method 300, according to an embodiment of the present disclosure. The method 300 may be implemented by the system 102 using components thereof, as described above. Further, for the sake of brevity, details of the present subject matter that are explained in detail with reference to description of FIGS. 1 and 2 above are not explained in detail herein.

At block 302, a heart rate of the individual during operation within the environment is measured. The environment, in an example, may be a closed space environment, such as a vehicle cabin, and airplane cockpit, an airplane passenger seating area, an office cabin, a workstation, and the like. In an example, the heart rate may be measured for a predetermined period, say two minutes or five minutes. In an example, the heart rate sensor 104 is configured to measure the heart rate.

At block 304, pressure data of the individual is outputted. The pressure data may include overall pressure associated with the individual, percentage of area covered by body parts of the individual, activated pressure cells, and the like. In an example, the pressure sensing platform 106 may output the pressure data of the individual. At block 306, image data of the individual is outputted. The image data may include a plurality of images of the individual. In an example, the image capturing device 108 may output the image data.

At block 308, an amount of fat of the individual in the image data is inferred. In an embodiment, one or more of facial recognition techniques, image processing techniques, machine learning models, may be implemented to infer the amount of fat of the individual. Without limitation, in an example, the fat of the individual may include the BMI of the individual. In an example, the processing unit 110 is configured to infer the amount of fat using the image data.

At block 310, the amount of fat of the individual is updated using the pressure data. In an embodiment, the amount of fat, as determined using the image data is verified by correlating it with the pressure data of the individual. Accordingly, in a case where discrepancy is observed, the amount of fat may be updated. In another case where no discrepancy is observed, the value of the amount of fat may not be altered, in the step of updation. In an example, the processing unit 110 is configured to update the amount of fat using the pressure data.

At step 312, a threshold for determining the health state of the individual is controlled using the amount of fat and the heart rate of the individual. The threshold, as used herein, indicates a threshold value of probability of the individual to have health issues. In an example, the controlling of the threshold may be inversely proportional to the measured heart rate and the amount of fat. In an example, the processing unit 110 is configured to control the threshold for determining the health state of the individual.

Figure 4:
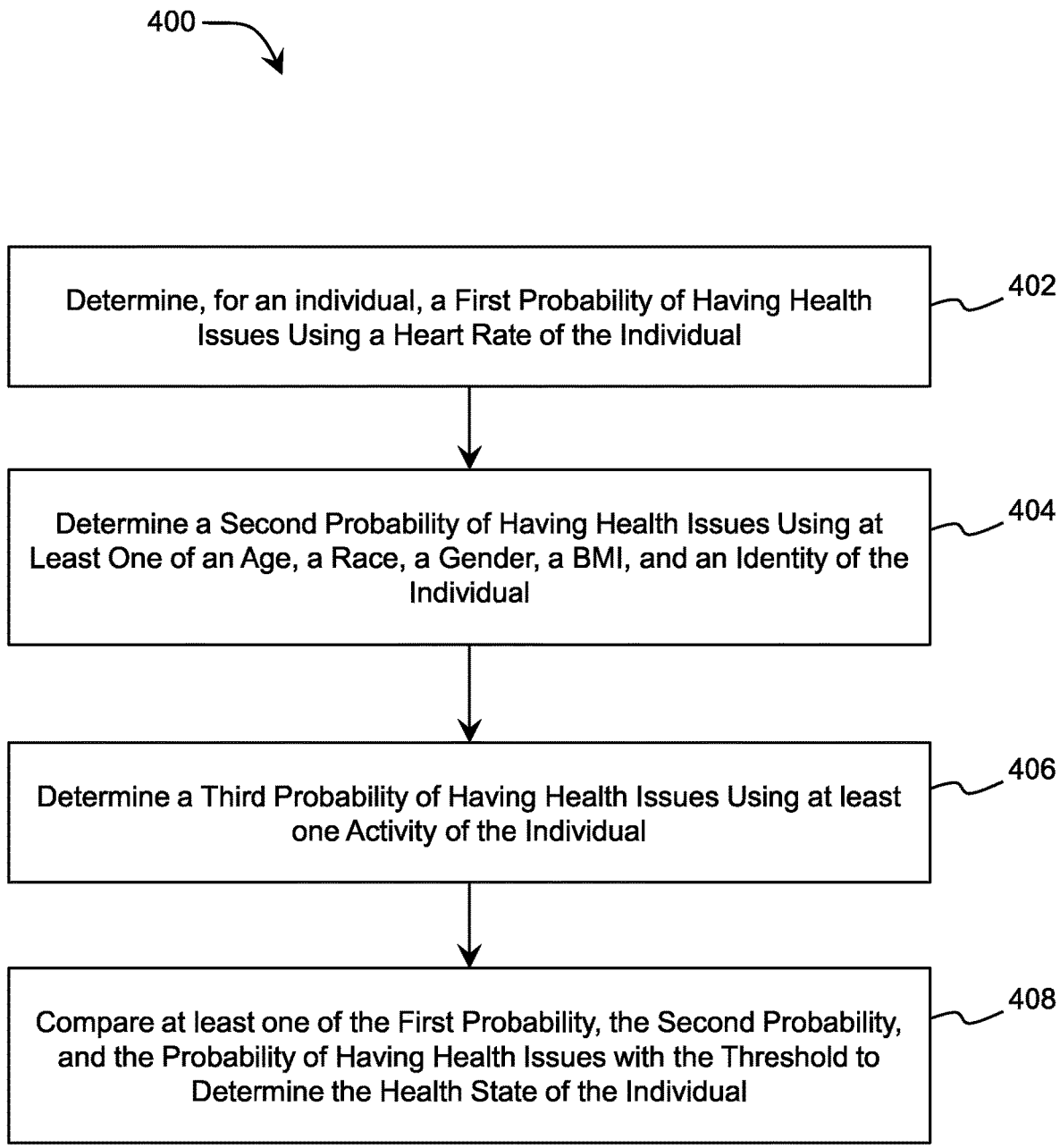
FIG. 4 illustrates a method of determining health state of individuals, according to an embodiment of the present subject matter.

FIG. 4 illustrates a method 400, according to an embodiment of the present disclosure. The method 400 may be implemented by the system 102 using components thereof, as described above. Further, for the sake of brevity, details of the present subject matter that are explained in detail with reference to description of FIGS. 1, 2, and 3 above are not explained in detail herein.

At block 402, for an individual, a first probability of having health issues is determined using the heart rate of the individual. In an implementation, at least one ML model may be implemented on the measured heart rate for determining the first probability of having health issues. In an example, the processing unit 110 may implement the at least one ML model and may determine the first probability.

At block 404, a second probability of having health issues is determined using at least one of an age, a race, a gender, a BMI, and an identity of the individual. In an example, at least one of the age, the race, the gender, and the identity of the individual is determined using the image data. The BMI of the individual is determined by using a set of features extracted from the image data and the pressure data. The set of features includes one or more face shape features, height features, and weight features, associated with the individual. Subsequently, a first database is queried using at least one of the age, the race, the gender, the BMI, and one or more preconditions associated with the identity of the individual to determine the second probability. The one or more preconditions are obtained by querying a second database using the identity of the individual. In an example, the processing unit 110 may determine the second probability.

At block 406, a third probability of having health issues is determined using at least one activity of the individual. In an example, determining, by the processing unit, a first value indicative of a facial activity of the individual is determined. Furthermore, a second value indicative of a body activity of the individual is determined. Subsequently, the third probability is determined based on the first value and the second value. In an example, the processing unit 110 may determine the third probability.

In an embodiment, at least one Machine Learning (ML) model may be implemented for determining at least one of the first probability, the second probability, and the third probability of having health issues.

At block 408, at least one of the first probability, the second probability, and the third probability of having health issues is compared with the threshold to determine the health state of the individual. In an example, the health state may be determined based on at least one of an ML model and a fuzzy logic technique. In an example, said model and techniques may be implemented for determining a short term health state and a grievous health state of the individual. In an example, the processing unit 110 may compare at least one of the first probability, the second probability, and the third probability of having health issues with the threshold, as explained above for determining the health state of the individual.

In an embodiment, in addition to the first probability, the second probability, and the third probability of having health issues, a movement of the individual may also be used for the determination of the health state of the individual. In said embodiment, the movement of the individual may be inferred based on the image data. Based on movement, it may be ascertained that whether the individual is stationary or moving, in a predetermined time period. Accordingly, the movement of the individual may be used in determining the health state, as explained above. In an example, the processing unit 110 may infer the movement, and may use the inferred movement for determining the health state of the individual.

Upon the determination of one or more health states, the determined health states may then be displayed to the individual.

Figure 5:
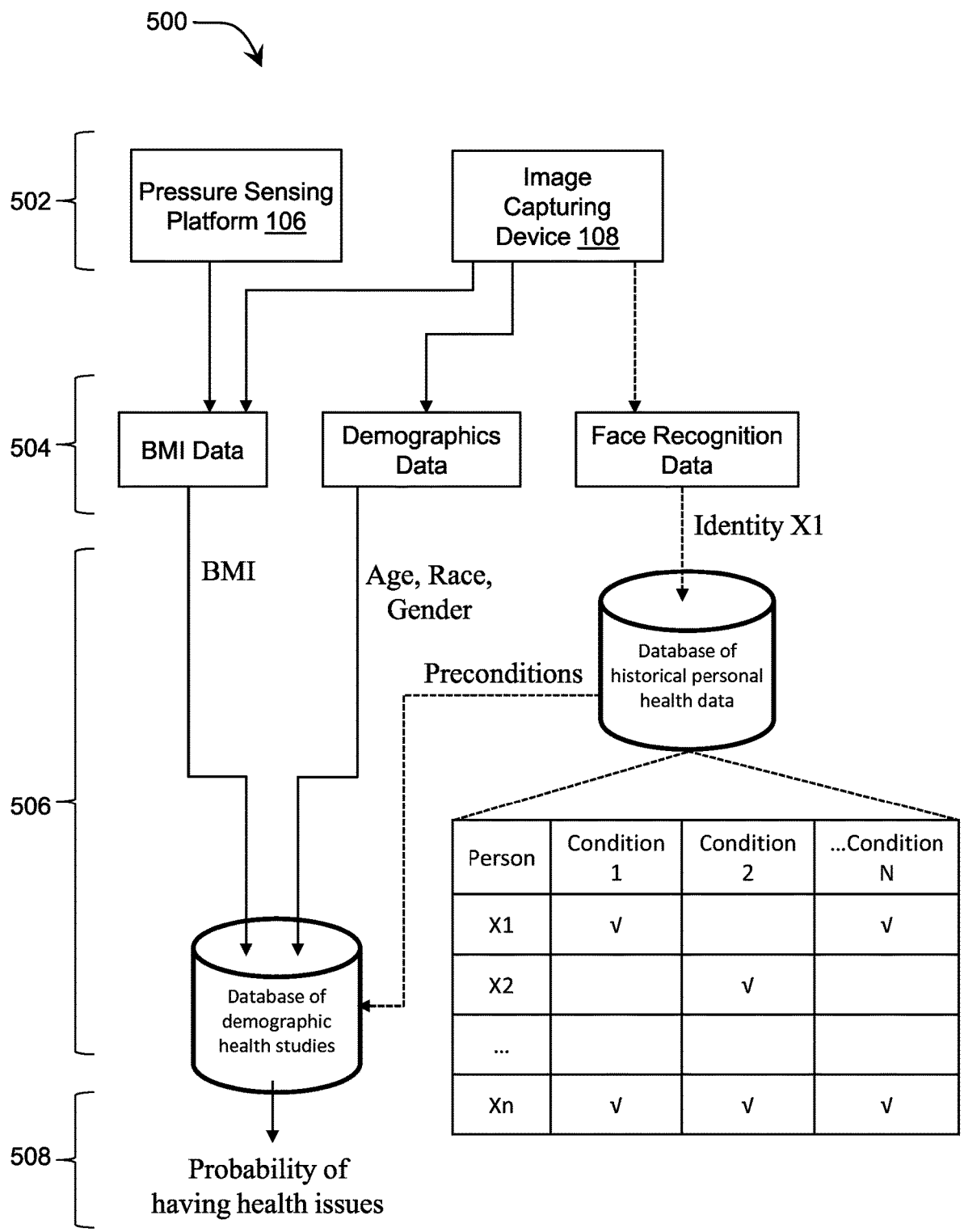
FIG. 5 illustrates an architectural flow diagram of determining probability of having health issues, according to an embodiment of the present subject matter.

FIG. 5 illustrates an architectural flow diagram 500 of determining a probability of having health issues, according to an embodiment of the present subject matter. As depicted, at step 502, the pressure sensing platform 106 is configured to output the pressure data associated with the individual and the image capturing device 108 is configured to output the image data associated with the individual. At step 504, based on the pressure data and the image data, BMI data including the BMI of the individual is generated. For generating the BMI data, one or more of facial recognition techniques, image processing techniques, and ML models may be implemented, in an example. Detailed description of determining the BMI is provided in FIG. 6 below.

Furthermore, at step 504, demographics data, for example, age, race, and gender, of the individual may be generated based on the image data of the individual. For generating the demographics data, one or more of facial recognition algorithms, ML models, image processing techniques, and demographics databases may be implemented. Furthermore, at step 504, face recognition data including an identity of the individual may be generated. For generating the face recognition data, one or more of facial recognition algorithms, ML models, image processing techniques, and user databases may be implemented.

At step 506, the probability of having health issues is determined by querying a database of demographic health studies based on the BMI, the age, the race, and the gender of the individual. In a further embodiment, where the individual is identified, the querying of the database may be further based on one or more preconditions associated with the individual. The preconditions include details of existing health conditions of the individual. In an example, the preconditions may be obtained by querying a database of historical personal health data based on the identity of the individual. In an embodiment, for the determination of the probability of having health issues, one or more ML models may be implemented.

Subsequently, at step 508, the probability of having health issues, as determined, is outputted.

Figure 6:
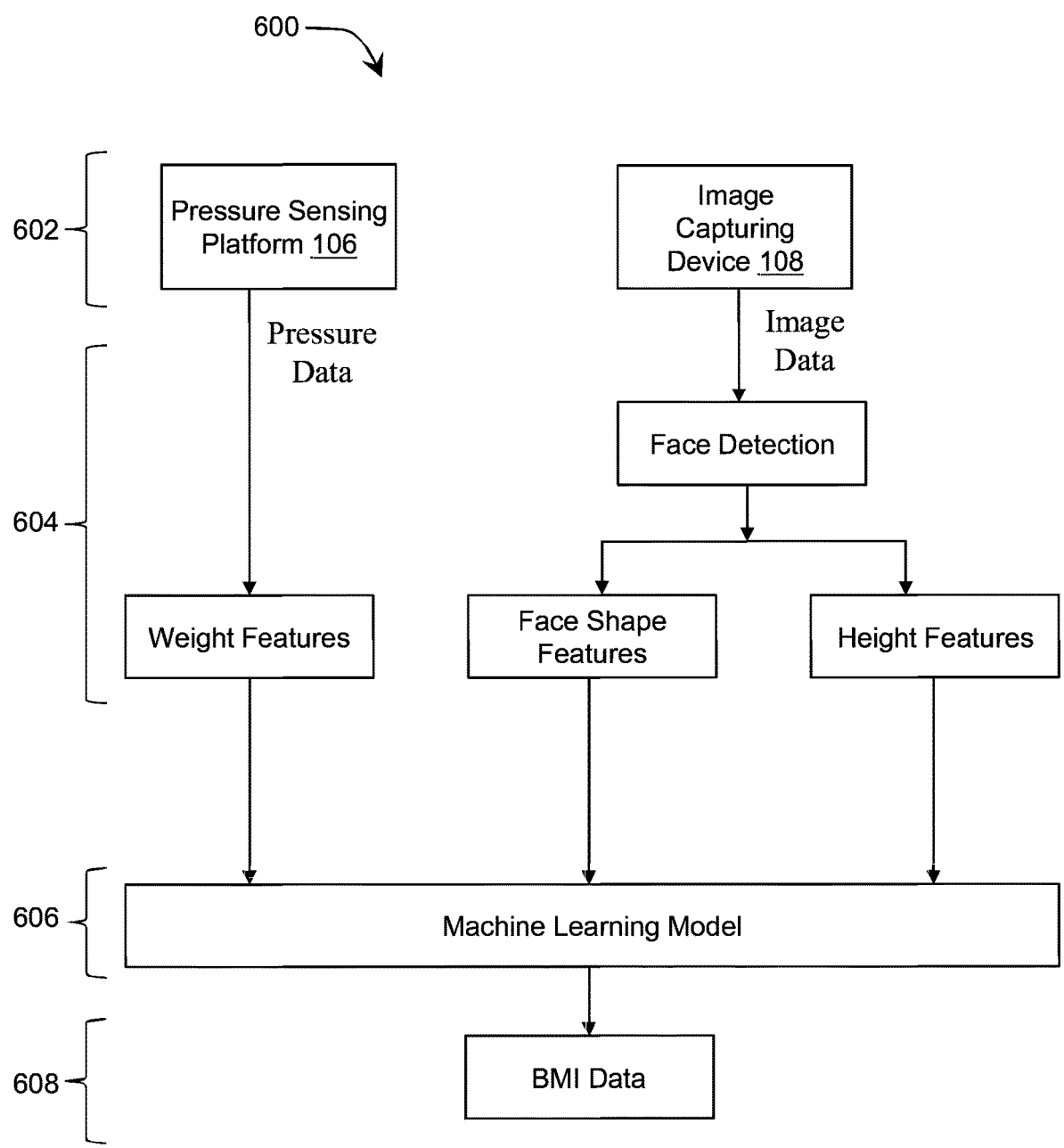
FIG. 6 depicts an architectural flow diagram of determining BMI, according to an embodiment of the present subject matter.

FIG. 6 depicts an architectural flow diagram 600 of determining BMI, according to an embodiment of the present subject matter. As depicted, at step 602, the pressure sensing platform 106 is configured to output pressure data associated with the individual and the image capturing device 108 is configured to output Image data associated with the individual.

At step 604, from the pressure data, weight features associated with the individual may be determined. In an example, the weight features may include, but are not limited to, an overall pressure, and percentage area covered by the body part(s) of the individual. The overall pressure may be determined by summing pressure readings from all the activated pressure cells of the pressure sensing platform 106. Similarly, based on the activated pressure cells and the non-activated pressure cells, the percentage area covered by the body part(s) of the individual may be determined.

Furthermore, at step 604, based on the image data, the individual's face in the image(s) is identified, for example, using a conventional object identification technique. Subsequently, face shape features and height features are determined. The face shape features, in an example, include information about the face alignment of the individual. In other words, the facial points of the individual are determined. Accordingly, information about the individual's jawline relative to the facial points may be determined. The aforementioned information serves as face shape features.

The height features include face position of the individual with respect to the image, in one example. In an example, conventional image processing and object identification techniques may be implemented for identifying the face position.

Subsequent to the aforementioned determinations, at step 606, the weight features, the face shape features, and the height features are provided as an input to an ML model.

In an embodiment, the ML model at first may infer the amount of fat of the individual based on the image data. Without limitation, as used herein, the amount of fat may be an inferred Body Mass Index (BMI) of the individual. Subsequently, the ML model may correlate the amount of fat as inferred, with the weight features. Accordingly, in one example, where there is a discrepancy between the amount of fat and the weight features, the amount of fat may be updated. In said example, the updation of the amount of fat may be done based on the pressure data, i.e., in other words, based on the weight features. In another example, where there is no discrepancy, the step of updation includes not changing the amount of fat.

Subsequently, at step 608, the BMI data is outputted. Without limitation, the BMI data may include the value of the amount of fat. In other words, the value of BMI is outputted. As would be appreciated, usage of BMI as an indicator of fat is not to be construed as limiting. In other example embodiments, other measurements indicative of the amount of fat may be used.

As mentioned above, the BMI of the individual may be used for determining the probability of having health issues.

Figure 7:
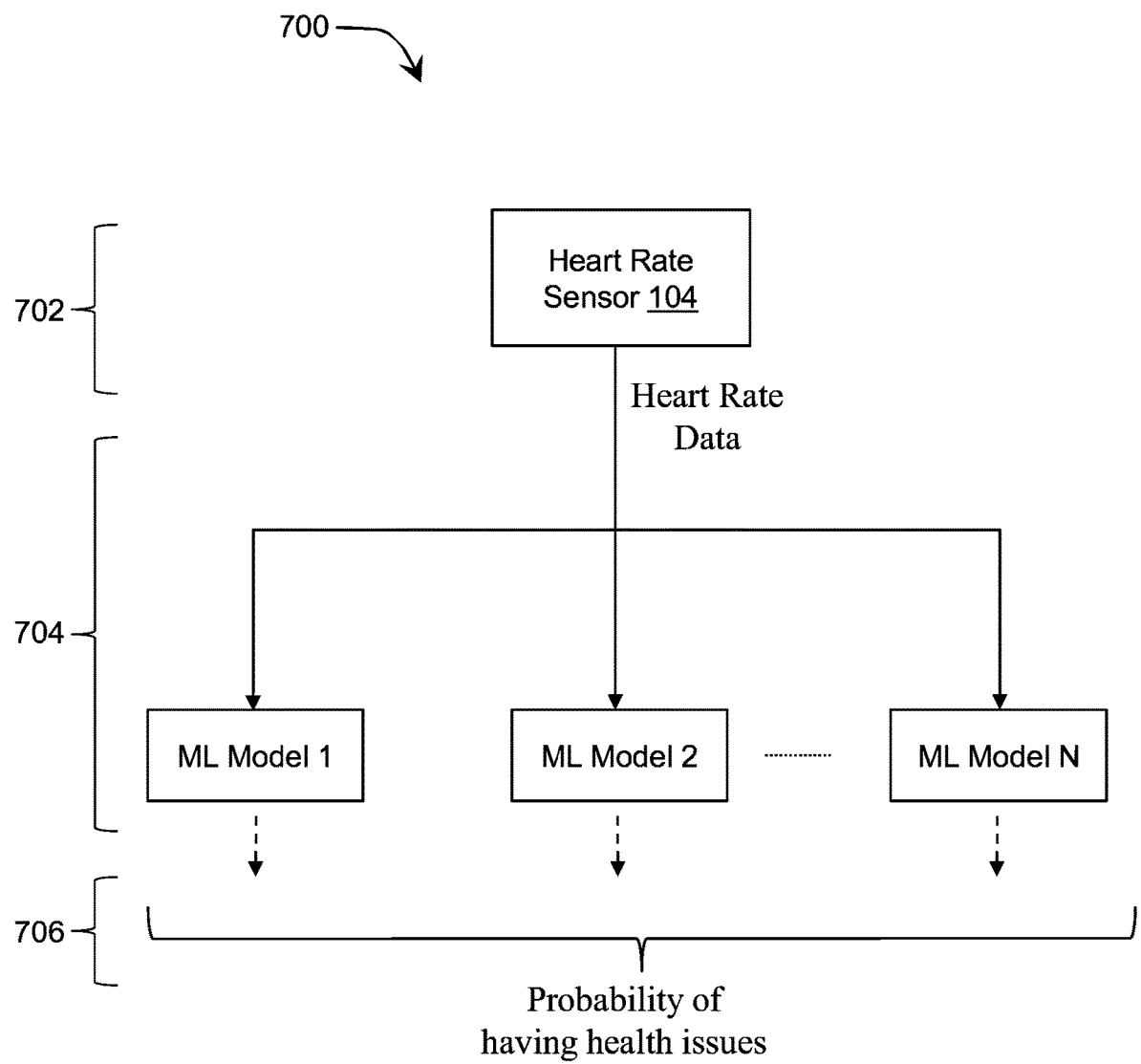
FIG. 7 illustrates an architectural flow diagram of determining probability of having health issues, according to an embodiment of the present subject matter.

FIG. 7 illustrates an architectural flow diagram 700 of determining a probability of having health issues, according to an embodiment of the present subject matter. As depicted, at step 702, the heart rate sensor 104 is configured to output the heart rate data corresponding to the individual. The heart rate data includes the heart rate readings of the individual, as measured over a predetermined period. At step 704, the heart rate data is subsequently provided to one or more ML models 1, 2, . . . , N. Each of the ML models 1 to N may analyze the heart rate and may determine the probability of having a health issue. As an example, the ML model 1 may determine the probability of sudden cardiac death based on the measured heart rate. The ML 2 may determine the probability of having hypertension, hyperlipidemia, and hyperglycemia, based on the measured heart rate.

At step 706, based on one or more of the aforementioned probabilities, the probability of having health issues is determined.

Figure 8:
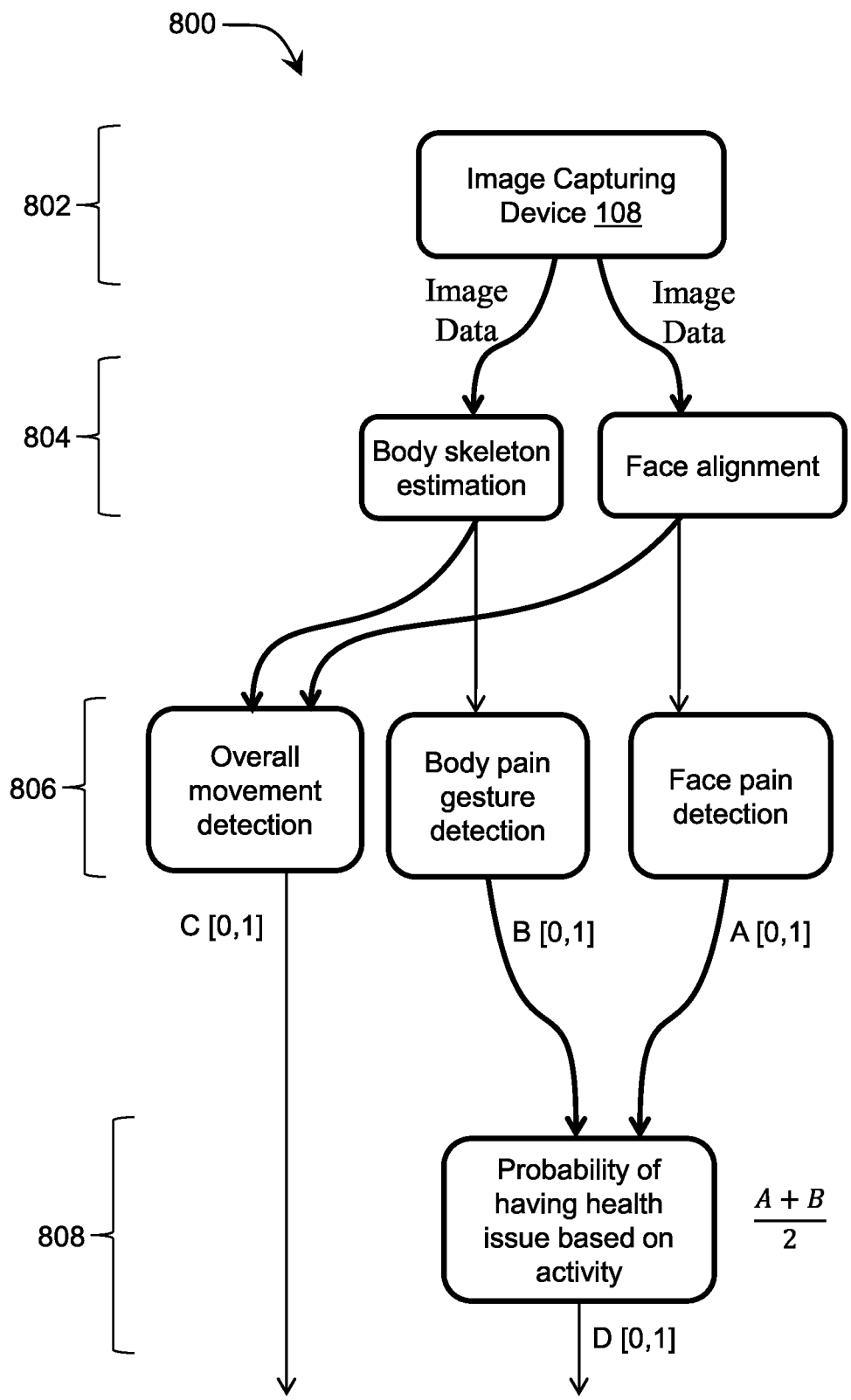
FIG. 8 illustrates an architectural flow diagram of determining probability of having health issues, according to an embodiment of the present subject matter.

FIG. 8 illustrates an architectural flow diagram 800 of determining a probability of having health issues, according to an embodiment of the present subject matter. As depicted, at step 802, the image capturing device 108 is configured to output the image data associated with the individual. The image data includes a plurality of images of the individual. At step 804, the image data is analyzed to determine the body skeleton estimation and the face alignment of the individual.

At 806, in an example, based on the alignment of the face, a face pain activity of the individual is detected. The face pain activity is represented as a continuous signal A, having a value between 0 and 1. Furthermore, at 806, based on the body skeleton estimation, a body pain gesture activity of the individual is detected. The body pain gesture activity is represented as a continuous signal B, having a value between 0 and 1.

Furthermore, at 806, the overall movement of the individual is determined based on the body skeleton estimation and face alignment of the individual. The overall movement may be outputted in terms of a continuous signal C, having a value between 0 and 1. As explained above, the overall movement of the individual may be used for determining the short term health state and the grievous health state of the individual.

At step 808, the probability of having health issues based on the activity is determined. In an example, said probability is determined by taking an average of A and B. Accordingly, a continuous signal D, having a value between 0 and 1, and indicative of the probability of having health issues is obtained.

Thus, as may be gathered from above, aspects of the present subject matter provides for an increased accuracy in determining health states of individuals. Furthermore, according to aspects described herein, a plurality of health states, such as short term health state and long term health state of the individuals may be determined. Furthermore, the present subject matter provides for a simple apparatus/device setup for implementing aspects described herein. Accordingly, such apparatuses/devices may be easily implemented in routine spaces/environments. Furthermore, aspects of the present subject matter may be implemented for with minimal or no intrusion/obstruction. Thus, minimal hindrance is caused to individuals being monitored.

Terms used in this disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description of embodiments, claims, or drawings, should be understood to contemplate the possibilities of including one of the terms, either of the terms or both terms. For example, the phrase "A or B" should be understood to include the possibilities of "A" or "B" or "A and B."

All examples and conditional language recited in this disclosure are intended for pedagogical objects to aid the reader in understanding the invention and the concepts contributed by the inventor to furthering the art and are to be construed as being without limitation to such specifically recited examples and conditions. Although embodiments of the present disclosure have been described in detail, it should be understood that various changes, substitutions, and alterations could be made thereto without departing from the spirit and scope of the present disclosure.

The invention claimed is:

1. A system to determine a health state of an individual in an environment, the system comprising:
   a heart rate sensor configured to measure a heart rate of the individual during operation within the environment;
   a pressure sensing platform configured to output pressure data of the individual;
   an image capturing device configured to output image data of the individual; and
   a processing unit, wherein the processing unit includes one or more machine learning (ML) models configured to analyze the heart rate, the image data, and the pressure data, and the processing unit is communicatively coupled to the heart rate sensor, the pressure sensing platform, and the image capturing device, wherein the processing unit is configured to:
      obtain an amount of fat of the individual based on the image data by the one or more ML models;
      verify the amount of fat of the individual by correlating it with the pressure data of the individual, in a case where a discrepancy is observed, update the amount of fat, and in a case where no discrepancy is observed, retain the amount of fat;
      control a threshold value for determining the health state of the individual, wherein the threshold value indicates a probability of the individual to have health issues, the threshold value is based on the heart rate and the amount of fat of the individual, and the threshold value is inversely proportional to the heart rate and the amount of fat; and
      determine possibilities of health issues of the individual by the one or more ML models with the threshold value.

2. The system as claimed in claim 1, wherein the processing unit is further configured to:
- determine a first probability of having health issues using the measured heart rate;
- determine a second probability of having health issues using at least one of an age, a race, a gender, a Body Mass Index (BMI), and an identity of the individual;
- determine a third probability of having health issues using at least one activity of the individual; and
- compare at least one of the first probability, the second probability, and the third probability of having health issues with the threshold value to determine the health state of the individual.

3. The system as claimed in claim 2, wherein the processing unit is further configured to:
- infer movement of the individual in the image data; and
- determine the health state of the individual using the movement of the individual.

4. The system as claimed in claim 2, wherein the processing unit is further configured to implement at least one of the one or more ML models for determining at least one of the first probability, the second probability, and the third probability of having health issues.

5. The system as claimed in claim 2, wherein the processing unit is further configured to:
- determine at least one of the age, the race, the gender, and the identity of the individual using the image data;
- determine the BMI of the individual using a set of features extracted from the image data and the pressure data, wherein the set of features comprises one or more face shape features, height features, and weight features, associated with the individual; and
- query a first database using at least one of the age, the race, the gender, the BMI, and one or more preconditions associated with the identity of the individual to determine the second probability.

6. The system as claimed in claim 5, wherein the processing unit is further configured to:
- query a second database based on the identity of the individual; and
- obtain the one or more preconditions associated with the individual from the second database.

7. The system as claimed in claim 2, wherein the processing unit is further configured to:
- determine a first value indicative of a facial activity of the individual;
- determine a second value indicative of a body activity of the individual; and
- determine the third probability based on the first value and the second value.

8. The system as claimed in claim 2, wherein the processing unit is further configured to determine the health state based on at least one of a fuzzy logic technique and the one or more ML models.

9. A method of determining a health state of an individual in an environment, the method comprising:
- measuring, by a heart rate sensor, a heart rate of the individual during operation within the environment;
- outputting, by a pressure sensing platform, pressure data of the individual;
- outputting, by an image capturing device, image data of the individual;
- obtaining, by a processing unit, wherein the processing unit includes one or more machine learning (ML) models configured to analyze the heart rate, the image data, and the pressure data, an amount of fat of the individual based on the image data by the one or more ML models;
- verifying, by the processing unit, the amount of fat of the individual by correlating it with the pressure data of the individual, in a case where a discrepancy is observed, updating the amount of fat, and in a case where no discrepancy is observed, retaining the amount of fat;
- controlling, by the processing unit, a threshold value for determining the health state of the individual, wherein the threshold value indicates a probability of the individual to have health issues, the threshold value is based on the heart rate and the amount of fat of the individual, and the threshold value is inversely proportional to the heart rate and the amount of fat; and
- determining, by the one or more ML models, possibilities of health issues of the individual with the threshold value.

10. The method as claimed in claim 9, further comprising:
- determining, by the processing unit, a first probability of having health issues using the measured heart rate;
- determining, by the processing unit, a second probability of having health issues using at least one of an age, a race, a gender, a Body Mass Index (BMI), and an identity of the individual;
- determining, by the processing unit, a third probability of having health issues using at least one activity of the individual; and
- comparing, by the processing unit, at least one of the first probability, the second probability, and the third probability of having health issues with the threshold to determine the health state of the individual.

11. The method as claimed in claim 10, further comprising:
- inferring, by the processing unit, movement of the individual in the image data; and
- determining, by the processing unit, the health state of the individual using the movement of the individual.

12. The method as claimed in claim 10, wherein the method further comprises, by the processing unit, implementing at least one of the one or more ML models-for determining at least one of the first probability, the second probability, and the third probability of having health issues.

13. The method as claimed in claim 10, further comprising:
- determining, by the processing unit, at least one of the age, the race, the gender, and the identity of the individual using the image data;
- determining, by the processing unit, the BMI of the individual using a set of features extracted from the image data and the pressure data, wherein the set of features comprises one or more face shape features, height features, and weight features, associated with the individual; and
- quering, by the processing unit, a first database using at least one of the age, the race, the gender, the BMI, and one or more preconditions associated with the identity of the individual to determine the second probability.

14. The method as claimed in claim 13, further comprising:
- querying, by the processing unit, a second database based on the identity of the individual; and
- obtaining, by the processing unit, the one or more preconditions associated with the individual from the second database.

15. The method as claimed in claim 10, further comprising:

determining, by the processing unit, a first value indicative of a facial activity of the individual;
determining, by the processing unit, a second value indicative of a body activity of the individual; and
determining, by the processing unit, the third probability based on the first value and the second value.

16. The method as claimed in claim 10, further comprising determining, by the processing unit, the health state based on at least one of a fuzzy logic technique and the one or more ML models.

17. A non-transitory computer-readable medium having embodied thereon a computer program for executing a method implementable by a system, wherein the method comprises:
measuring, by a heart rate sensor, a heart rate of the individual during operation within the environment;
outputting, by a pressure sensing platform, pressure data of the individual;
outputting, by an image capturing device, image data of the individual;
obtaining, by a processing unit, wherein the processing unit includes one or more machine learning (ML) models configured to analyze the heart rate, the image data, and the pressure data, an amount of fat of the individual based on the image data by the one or more ML models;
verifying, by the processing unit, the amount of fat of the individual by correlating it with the pressure data of the individual, in a case where a discrepancy is observed, updating the amount of fat, and in a case where no discrepancy is observed, retaining the amount of fat;
controlling, by the processing unit, a threshold value for determining the health state of the individual, wherein the threshold value indicates a probability of the individual to have health issues, the threshold value is based on the heart rate and the amount of fat of the individual, and the threshold value is inversely proportional to the heart rate and the amount of fat; and
determining, by the one or more ML models, possibilities of health issues of the individual with the threshold value.

18. The non-transitory computer-readable medium as claimed in claim 17, wherein the method further comprises:
determining, by the processing unit, a first probability of having health issues using the measured heart rate;
determining, by the processing unit, a second probability of having health issues using at least one of an age, a race, a gender, a Body Mass Index (BMI), and an identity of the individual;
determining, by the processing unit, a third probability of having health issues using at least one activity of the individual; and
comparing, by the processing unit, at least one of the first probability, the second probability, and the third probability of having health issues with the threshold to determine the health state of the individual.

19. The non-transitory computer-readable medium as claimed in claim 17, wherein the method further comprises:
inferring, by the processing unit, movement of the individual in the image data; and
determining, by the processing unit, the health state of the individual using the movement of the individual.

20. The non-transitory computer-readable medium as claimed in claim 17, wherein the method further comprises, implementing, by the processing unit, at least one of the one or more ML models for determining at least one of the first probability, the second probability, and the third probability of having health issues.

* * * * *